(12) United States Patent
Marston et al.

(10) Patent No.: US 6,284,760 B1
(45) Date of Patent: Sep. 4, 2001

(54) METHOD OF TREATING SCHIZOPHRENIA, DEPRESSION AND OTHER NEUROLOGICAL CONDITIONS

(75) Inventors: Hugh M. Marston, East Lothian; John S. Kelly, Edinburgh, both of (GB)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/331,185

(22) PCT Filed: Dec. 19, 1997

(86) PCT No.: PCT/JP97/04704

§ 371 Date: Jun. 24, 1999

§ 102(e) Date: Jun. 24, 1999

(87) PCT Pub. No.: WO98/27930

PCT Pub. Date: Jul. 2, 1998

(30) Foreign Application Priority Data

Dec. 24, 1996 (AU) ........................................... 4389
Dec. 24, 1996 (AU) ........................................... 4391
Apr. 3, 1997 (AU) ........................................... 5451

(51) Int. Cl.$^7$ .................................................. A61K 31/495
(52) U.S. Cl. ........................................................ 514/255.01
(58) Field of Search ......................................... 514/255.01

(56) References Cited

U.S. PATENT DOCUMENTS 5,250,528 * 10/1993 Oku et al. ............................ 514/252

* cited by examiner

Primary Examiner—William R. A. Jarvis
(74) Attorney, Agent, or Firm—Oblon, Spivak, McClelland, Maier & Neustadt, P.C.

(57) ABSTRACT

This application relates to the use of aminopiperazine derivatives for the treatment of schizophrenia, depression, and other neurological conditions.

31 Claims, No Drawings

METHOD OF TREATING SCHIZOPHRENIA, DEPRESSION AND OTHER NEUROLOGICAL CONDITIONS

This application is a 371 of PCT/JP97/04704, filed Dec. 19, 1997.

BACKGROUND OF THE INVENTION

1. Field of the Invention

This invention relates to a new use of aminopiperazine derivatives and pharmaceutically acceptable salts thereof for the treatment and/or prevention of schizophrenia, depression, stroke; head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism in mammals

2. Description of the Background

The aminopiperazine derivatives used in this invention are known as described in PCT International Publication No. WO 91/01979 that said aminopiperazine derivatives possess the potentiation of the cholinergic activity and are useful in the treatment of disorders in the central nervous system for human beings, and more particularly in the treatment of amnesia, dementia, senile dementia and the like.

SUMMARY OF THE INVENTION

The present invention relates to a new use of aminpiperazine derivatives and pharmaceutically acceptable salts thereof for the treatment and/or prevention of schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism for mammals.

Accordingly, this invention is to provide a new use of aminopiperazine derivatives and pharmaceutically acceptable salts thereof for treating and/or preventing schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

Further, this invention is to provide an agent and a pharmaceutical composition for treating and/or preventing schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism, which comprises said aminopiperazine derivatives and pharmaceutically acceptable salt thereof.

Still further, this invention is to provide a therapeutic method for the treatment and/or prevention of schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism, which comprises administering said said aminopiperazine derivatives and pharmaceutically acceptable salts thereof to mammals.

DETAILED DESCRIPTION OF THE PREFERRED EMBODIMENTS

The aminopiperazine derivatives used in this invention can be represented by the following general formula la [I]:

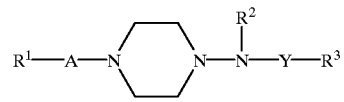

wherein $R^1$ is lower alkyl, aryl, ar(lower)alkoxy or a heterocyclic group, each of which may be substituted with halogen, $R^2$ is hydrogen or lower alkyl, $R^3$ is cyclo(lower)alkyl, aryl or ar(lower)alkyl, each of which may be substituted with halogen, A is

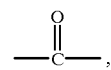

—SO$_2$— or lower alkylene, and

Y is

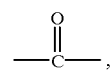

—SO$_2$— or

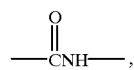

and pharmaceutically acceptable salts thereof.

Said compound (I) and pharmaceutically acceptable salts thereof are useful in the treatment and/or prevention of schizophrenia, depression, stroke, head injury, nicotine withdrawal, spinal cord injury, anxiety, pallkiuria, incontinence of urine, myotonic dystrophy, attention deficit hyperactivity disorder, excessive daytime sleepiness (narcolepsy), Parkinson's disease or autism in mammals.

Particulars of the various definitions mentioned in this specification and preferred examples thereof are explained in the following.

The term "lower" is intended to mean a group having 1 to 6 carbon atom(s), unless otherwise provided.

Suitable "lower alkyl" may be a straight or branched one such as methyl, ethyl, propyl, isopropyl, butyl, isobutyl, tert-butyl, pentyl, hexyl, or the like, in which preferable one is methyl.

Suitable "aryl" may be phenyl, naphthyl, tolyl, xylyl, mesityl, cumenyl, and the like, Ln which preferable one is phenyl or naphthyl.

Suitable "ar(lower)alkoxy" may be benzyloxy, phenethyloxy, phenylpropoxy, benzhydryloxy, trityloxy and the like.

Suitable "heterocyclic group" may include saturated or unsaturated, monocyclic or polycyclic one containing at least one hetero atom such as nitrogen atom, oxygen atom or sulfur atom.

The preferred examples of thus defined "heterocyclic group" may be an unsaturated, 3 to 8-membered, more preferably 5 or 6-membered heteromonocyclic group containing 1 to 4-nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

unsaturated, condensed heterocyclic group containing 1 to 5 nitrogen atom(s), for example, indolyl, isoindolyl, indolizinyl, benzimidazolyl, quinolyl, isoquinolyl, indazolyl, benzotriazolyl, etc.;

unsaturated, 3 to 8-membered heteromonocyclic group containing 1 to 2 oxygen atom(s) and 1 to 3 nitrogen atom(s), for example, oxazolyl, isoxazolyl, oxadiazolyl, etc.;

saturated, 3 to 8-membered heteromonocyclic group containing 1 to 2 oxygen atom(s) and 1 to 3 nitrogen atom(s), for example, morpholino, sydnonyl, etc.;

unsaturated, condensed heterocyclic group containing 1 to 2 oxygen atom(s) and 1 to 3 nitrogen atom(s), for example, benzoxazolyl, benzoxadiazolyl, etc.;

unsaturated, 3 to 8-membered heteromonoyclcic group containing 1 to 2 sulfur atom(s) and 1 to 3 nitrogen atom(s), for example, thiazolyl, isothiazolyl, thiadiazolyl, etc.;

unsaturated, 3 to 8-membered heteromonocyclic group containing 1 to 2 sulfur atom(s), for example, thienyl, etc.;

unsaturated, condensed heterocyclic group containing 1 to 2 sulfur atom(s) and 1 to 3 nitrogen atom(s), for example, benzothiazolyl, benzothiadiazolyl, etc.;

unsaturated, 3 to 8-membered heteromonocyclic group containing an oxygen atom, for example, furyl, etc.;

unsaturated, condensed heterocyclic group containing 1 to 2 sulfur atom(s), for example, benzothienyl, etc.;

unsaturated, condensed heterocyclic group containing 1 to 2 oxygen atom(s), for example, benzofuranyl, etc.; or the like.

Suitable "cyclo(lower)alkyl" may be cyclopropyl, cyclobutyl, cyclopentyl, cyclohexyl, and the like.

Suitable "ar(lower)alkyl" may be benzyl, phenethyl, phenylpropyl, benzhydryl, trityl, and the like.

Suitable "lower alkylene" may be methylene, ethylene, propylene, pentamethylene, hexamethylene, and the like.

The above-mentioned "lower alkyl", "aryl", "ar(lower) alkoxy", "heterocyclic group", "cyclo(lower)alkyl" and "ar (lower)alkyl" may be substituted with halogen [e.g. fluorine, chlorine, bromine and iodine].

Preferred compound [I] is one which has a lower alkyl, phenyl, naphthyl or thienyl for $R^1$, hydrogen or lower alkyl for $R^2$, phenyl which may be substituted with a halogen for $R^3$,

for A, and

or —SO$_2$— for Y.

More preferred compound [I] is one which has a lower alkyl for R hydrogen for $R^2$, phenyl which is substituted with a halogen for $R^3$,

for A, and

for Y.

Most preferred compound [I] is N-(4-acetyl-1-piperazinyl)-4-fluorobenzamide.

Suitable pharmaceutically acceptable salts of the compound [I] are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. aspartic acid salt, glutamic acid, salt, etc.] and the like.

It is to be noted that the compound [I] may include one or more stereoisomer(s) due to asymmetric carbon atoms, and all of such isomers and mixture thereof are included within the scope of this invention.

Additionally, it is to be noted that any hydrate of the compound [I] is also included within the scope of this invention.

Now in order to show the utility of the compound [I] and pharmaceutically acceptable salts thereof in this invention, the pharmacological test was carried out and its abstract is shown in the following.

The effect of the compound [I] upon cognitive function was examined using an operant delayed non-match to place paradigm (DNMTP) task which is shown to be disrupted dose-dependently by the administration of haloperidol. The following interactions were explored: haloperidol plus amphetamine, haloperidol plus the compound [I] and haloperidol plus the compound [I] and amphetamine. Neither a low dose of amphetamine nor two doses of the compound [I] when administered with haloperidol, or alone, altered the profile of performance relative to control. The experiments with haloperidol and the compound [I] plus amphetamine revealed a profound attenuation of the deficits associated with increasing doses of haloperidol by the larger dose of the compound [I].

These experiments confirmed that the compound [I] has a specific effect on dopaminergic status which appears to be state dependent and is useful for treating and/or preventing schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Examples is given for the purpose of illustrating this invention.

EXAMPLE 1

| (Capsule) | |
|---|---|
| N-(4-Acetyl-1-piperazinyl)-4-fluorobenzamide | 5 mg |
| Lactose | 80 mg |

The above-mentioned ingredients were mixed and the mixture was encapsulated to provide the capsule.

What is claimed is:

1. A method of treating or preventing schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism in a mammal, which comprises administering an effective amount of at least one of the following compounds of the formula (I) to a mammal in need thereof:

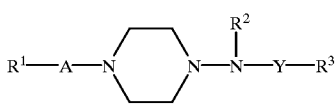

(I)

wherein:
R$^1$ is lower alkyl, aryl, ar(lower)alkoxy or a heterocyclic group, each of which is optionally substituted with halogen;
R$^2$ is hydrogen or lower alkyl;
R$^3$ is cyclo(lower)alkyl, aryl or ar(lower)alkyl, each of which is optionally substituted with halogen;
A is

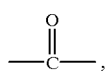

,

—SO$_2$— or lower alkylene; and
Y is

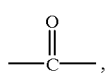

,

—SO$_2$— or

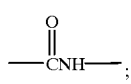

;

or a pharmaceutically acceptable salt or hydrate thereof.

2. The method of claim 1, wherein said mammal is human.

3. The method of claim 1, wherein in the formula (I), said heterocyclic group is a 3 to 8-membered heterocyclic group containing at least one heteroatom selected from the group consisting of nitrogen, oxygen and sulfur atom.

4. The method of claim 3, wherein in the formula (I), said heterocyclic group is a 5 or 6-membered heteromonolic group containing 1 to 4 nitrogen atoms.

5. The method of claim 4, wherein in the formula (I), said 5 or 6-membered heterocyclic group is selected from the group consisting of pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, and tetrazolyl.

6. The method of claim 3, wherein in the formula (I), said heterocyclic group is selected from the group consisting of indolyl, isoindolyl, indolizinyl, benzimidazolyl, quinolyl, isoquinolyl, indazolyl, and benzotriazoyl.

7. The method of claim 1, wherein in the formula (I), said heterocyclic group is a 3 to 8-membered heterocyclic group containing 1 to 2 oxygen atoms and 1 to 3 nitrogen atoms.

8. The method of claim 7, wherein in the formula (I), said heterocyclic group is selected from the group consisting of oxazolyl, isoxazolyl, oxadiazolyl, and morpholino.

9. The method of claim 3, wherein in the formula (I), said heterocyclic group is benzoxazolyl or benzoxadiazolyl.

10. The method of claim 3, wherein in the formula (I), said heterocyclic group contains 1 to 2 sulfur atoms, and 1 to 3 nitrogen atoms.

11. The method of claim 10, wherein in the formula (I), said heterocyclic group is selected from the group consisting of thiazolyl, isothiazolyl and thiadiazolyl.

12. The method of claim 3, wherein the formula (I), said heterocyclic group contains 1 to 2 sulfur atoms.

13. The method of claim 12, wherein in the formula (I), said heterocyclic group is thienyl.

14. The method of claim 1, wherein in the formula (I), said heterocyclic group is selected from the group consisting of benzothiazolyl, benzothiadiazolyl, furyl, benzothienyl, and benzofuranyl.

15. The method of claim 1, wherein in the formula (I), said aryl of R$^1$ and R$^3$ is independently selected from the group consisting of phenyl, naphthyl, tolyl, xylyl, mesityl and cumenyl.

16. The method of claim 1, wherein in the formula (I), said ar(lower)alkyl of R$^3$ is benzyl, phenethyl, phenylpropyl, benzhydryl or trityl.

17. The method of claim 1, wherein in the formula (I), said ar(lower)alkoxy of R$^1$ is benzyloxy, phenethyloxy, phenylpropoxyl, benzhydryloxy or trityloxy.

18. The method of claim 1, wherein in the formula (I), R$^1$ is lower alkyl, phenyl, naphthyl or thienyl.

19. The method of claim 1, wherein in the formula (I), R$^2$ is hydrogen or lower alkyl.

20. The method of claim 1, wherein in the formula (I), R$^3$ is phenyl optionally substituted with halogen.

21. The method of claim 1, wherein in the formula (I), A is

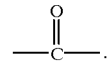

.

22. The method of claim 1, wherein in the formula (I), Y is

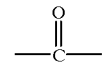

or —SO$_2$.

23. The method of claim 1, wherein in the formula (I), R$_1$ is lower alkyl, R$^2$ is hydrogen, R$^3$ is phenyl substituted with halogen, A is

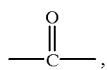

and Y is

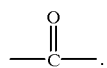

24. The method of claim 1, wherein the compound of the formula (I) is a hydrate.

25. The method of claim 24, wherein the hydrate is a monohydrate.

26. The method of claim 1, wherein the compound of the formula (I) is N-(4-acetyl-1-piperazinyl)-4-fluorobenzamide hydrate.

27. The method of claim 26, wherein the compound of the formula (I) is N-(4-acetyl-1-piperazinyl)-4-fluorobenzamide monohydrate.

28. The method of claim 1, wherein said salt of the compound of the formula (I) is an inorganic or organic addition salt.

29. The method of claim 1, which further comprises administering an effective amount of amphetamine to said mammal.

30. A pharmaceutical composition, which comprises:

a) an effective amount of at least one compound of claim 1, and b) an effective amount of amphetamine.

31. The pharmaceutical composition of claim 30, which further comprises a pharmaceutically-acceptable carrier.

* * * * *

UNITED STATES PATENT AND TRADEMARK OFFICE
CERTIFICATE OF CORRECTION

PATENT NO.   : 6,284,760 B1
DATED        : September 4, 2001
INVENTOR(S)  : Marston et al.

It is certified that error appears in the above-identified patent and that said Letters Patent is hereby corrected as shown below:

<u>Title page,</u>
Item [30], the Foreign Application Priority Data should read, -- [30]   Foreign Application Priority Data

Dec. 24, 1996  (AU) .....................................PO4389
Dec. 24, 1996  (AU) ....................................PO4391
Mar.  4, 1997  (AU) ..................................... PO5451 --

Signed and Sealed this

Fourteenth Day of May, 2002

*Attest:*

*Attesting Officer*

JAMES E. ROGAN
*Director of the United States Patent and Trademark Office*